United States Patent [19]
Goh et al.

[11] Patent Number: 5,527,818
[45] Date of Patent: Jun. 18, 1996

[54] SULFAMOYLTRIAZOLE DERIVATIVES OF FUNGICIDAL COMPOSITION CONTAINING SAME AS EFFECTIVE COMPONENT THEREOF

[75] Inventors: Atsushi Goh; Yoshihiro Usui; Yoshimi Tsutsumi; Yoshie Kirio; Yoshihiro Takayama; Seiichiro Yamada; Masako Yamanaka, all of Inashiki-gun, Japan

[73] Assignee: Mitsubishi Chemical Corporation, Tokyo, Japan

[21] Appl. No.: 199,218

[22] PCT Filed: Jul. 8, 1993

[86] PCT No.: PCT/JP93/00939

§ 371 Date: Mar. 4, 1994

§ 102(e) Date: Mar. 4, 1994

[87] PCT Pub. No.: WO94/01419

PCT Pub. Date: Jan. 20, 1994

[30] Foreign Application Priority Data

Jul. 14, 1992 [JP] Japan ..................... 4-186869

[51] Int. Cl.$^6$ ............... A01N 43/653; C07D 247/12; C07D 403/12; C07D 401/12
[52] U.S. Cl. ............... 514/384; 514/212; 514/318; 514/326; 514/340; 540/603; 546/193; 546/210; 546/272.4; 548/263.2; 548/264.2; 548/264.4
[58] Field of Search ............... 514/212, 318, 514/326, 340, 384; 540/603; 546/193, 210, 276; 548/263.2, 264.2, 264.4

[56] References Cited

U.S. PATENT DOCUMENTS

5,045,557  9/1991  Buss et al. ............... 514/398

*Primary Examiner*—Patricia L. Morris
*Attorney, Agent, or Firm*—Oblon, Spivak, McClelland, Maier & Neustadt

[57] ABSTRACT

The present invention relates to a sulfamoyl triazole derivative and a fungicide containing same as an effective component, the sulfamoyl triazole derivative being expressed by general formula (I):

$$A+O+_pS(=O)_2-\underset{N=}{\overset{N}{\underset{\|}{C}}}-N-S(=O)_2-N\begin{pmatrix}R^1\\R^2\end{pmatrix} \quad (I)$$

in which $R^1$ and $R^2$ are the same or different lower alkyl groups or an alkylene chain formed by integrating $R^1$ and $R^2$ and having 3 to 6 carbon atoms which may be substituted by a lower alkyl group; p is an integer 0 or 1; and A is a substituted aryl group.

The fungicide does not damage field and garden plants and it is effective for preventing and curing various disease injury at very small dosages.

8 Claims, No Drawings

SULFAMOYLTRIAZOLE DERIVATIVES OF FUNGICIDAL COMPOSITION CONTAINING SAME AS EFFECTIVE COMPONENT THEREOF

FIELD OF INVENTION

The present invention relates to a novel sulfamoyltriazole derivatives and a novel fungicidal composition same as an effective component thereof.

PREVIOUS ART

Japanese Patent Application Laid-Open No. 63-255269 discloses that sulfamoyltriazole derivatives having a specific structure can be used as an effective component of an antifungal agent.

However, the fungicidal activity of the foregoing conventional compounds has been unsatisfactory.

DISCLOSURE OF THE INVENTION

The inventors of the present invention have earnestly studied a variety of substituted sulfamoyltriazole type compounds to develop an agricultural fungicide having high fungicidal activity and excellent safety. As a result, it was found that sulfamoyltriazole derivatives having a triazole ring including a third carbon atom which is substituted by a specific aryl sulfonic group or an aryl oxysulfonic group are novel fungicides which do not damage field and garden plants and which exhibits excellent effects of preventing and curing various disease injury at very small dosages.

(SUMMARY OF THE INVENTION)

According to the present invention, there is provided a sulfamoyltriazole derivative and a fungicide containing same as an effective component thereof, the sulfamoyltriazole derivative being expressed by general formula (I):

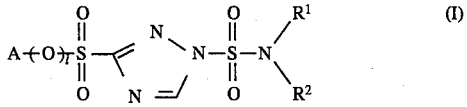

in which $R^1$ and $R^2$ are the same or different lower alkyl groups or an alkylene chain formed by integrating $R^1$ and $R^2$ and having 3 to 6 carbon atoms which may be substituted by a lower alkyl group; is an integer 0 or 1; and A is expressed by any one of the following substances:

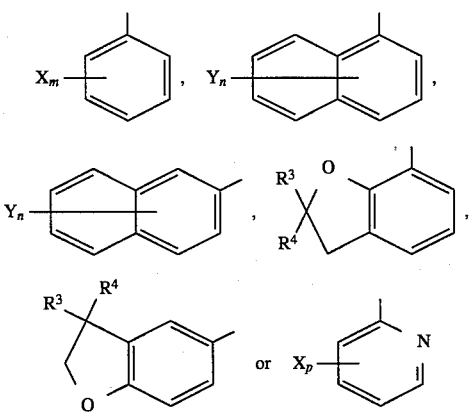

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m Is an integer 1, 2, 3, 4 or 5, Y is a hydrogen atom, a halogen atom, a lower alkyl group, a lower alkenyl group, a lower alkoxy group, a lower haloalkyl group, a lower haloalkoxy group, a lower alkylcarbonyl group, a formyl group, a lower alkoxycarbonyl group, a nitro group, a cyano group or an acetylamino group; n is an integer 1, 2, 3, 4 or 5; $R^3$ and $R^4$ are the same or different hydrogen atoms or lower alkyl groups; and p is an integer 1, 2, 3 or 4.

(CONCRETE DESCRIPTION OF THE INVENTION)

[I] Sulfamoyl Triazole Derivative

The sulfamoyltriazole derivatives according to the present invention and expressed by general formula (I) are described in detail below.

Atoms and groups of the compounds expressed in the general formula (I) expressed by $R^1$, $R^2$, $R^3$, $R^4$, X and Y defined as described above are exemplified as follows:

Lower Alkyl Group

A lower alkyl group having one to four carbon atoms, such as a methyl group, an ethyl group, an n-propyl group, an isopropyl group, an n-butyl group, an isobutyl group, a secondary butyl group, etc.

Halogen Atom

For example, fluorine, chlorine or bromine.

Lower Alkenyl Group

A lower alkenyl group having two to four carbon atoms such as an allyl group, a 2-methyl-2-propenyl group, a 2-butenyl group, a 3-butenyl group, etc.

Lower Alkoxy Group

A lower alkoxy group having one to four carbon atoms such as a methoxy group, an ethoxy group, an n-propoxy group, an isopropoxy group, an n-butoxy group, an isobutoxy group, a secondary butoxy group, a tert-butoxy group, etc.

Lower Haloalkyl Group

A lower haloalkyl group having one to three carbon atoms such as a dichloromethyl group, a trichloromethyl group, a difluoromethyl group, a trifluoromethyl group, a 2-chloroethyl group, a 2-fluoroethyl group, etc.

Lower Haloalkoxy Group

A lower haloalkoxy group having one to three carbon atoms such as a difluoromethoxy group, a trifluoromethoxy group, a 2-chloroethoxy group, 2-2-dichloroethoxy group, a 2,2,2-trichloroethoxy group, a 2-fluoroethoxy group, a 3-bromopropoxy group, etc.

Lower Alkyl Carbonyl Group

A lower alkylcarbonyl group having two to four carbon atoms such as a methylcarbonyl group, an ethylcarbonyl group, an n-propylcarbonyl group, an isopropylcarbonyl group, etc.

Lower Alkoxy Carbonyl Group

A lower alkoxycarbonyl group having two to four carbon atoms such as a methoxycarbonyl group, an ethoxy carbonyl group, an n-propoxycarbonyl group, an isopropoxy carbonyl group, etc.

Groups that are not exemplified above may be selected from the foregoing atoms and groups as to be combined arbitrarily or selected according to generally known common sense.

The lower alkyl groups denoted by $R^1$ and $R^2$ in general formula (I) are preferably methyl groups, ethyl groups, n-propyl groups or isopropyl groups.

The lower alkyl groups denoted by $R^3$ and $R^4$ are preferably methyl groups, ethyl groups or n-propyl groups.

It is preferable that the halogen atoms denoted by X and Y be fluorine atoms or chlorine atoms, the lower alkyl group be a methyl group, an ethyl group, an n-propyl group or an isopropyl group, the lower haloalkyl group be a trichloromethyl group or a trifluoromethyl group, and the lower haloalkoxy group be a difluoromethoxy group, a trifluoroethoxy group or a tetrafluoroethoxy group. It is preferable that m be 1, 2, 3 or 4, n be 1, 2 or 3 and p be 1, 2 or 3.

It Is preferable that A be the phenyl group substituted by the foregoing substituent, such as a 2,4-dichloro-3-methylphenyl group, a 4-trifluoromethylphenyl group, a 3-chlorophenyl group, a 2,3-dichlorophenyl group, a 2-chloro-4-trifluoromethylphenyl group, a 4-chlorophenyl group and a 3-trifluoromethylphenyl group.

The specific structure of the compounds according to the present invention and expressed by general formula (I) will now be exemplified.

(1) If l in general formula (I) is 1:

(i) General formula (I-1)

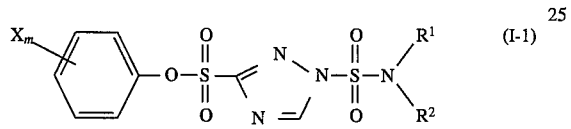

in which $R^1$, $R^2$, X and m are the same as in general formula (I).

(ii) General Formula (I-2)

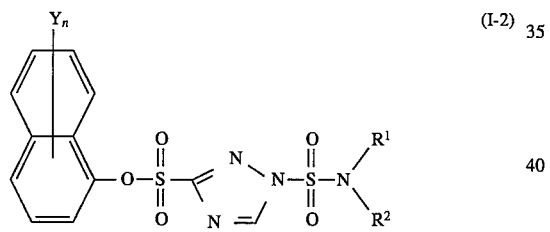

in which, $R^1$, $R^2$, Y and n are the same as in general formula (I).

(iii) General formula (I-3)

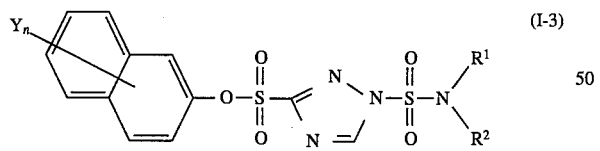

in which $R^1$, $R^2$, Y and n are the same as in general formula (I).

(iv) General formula (I-4)

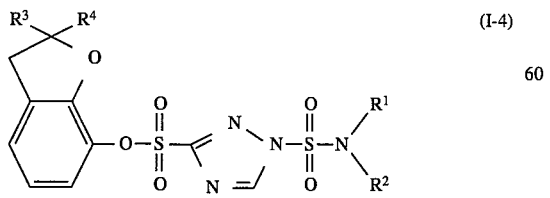

in which $R^1$, $R^2$, $R^3$ and $R^4$ are the same as in general formula (I).

(v) General formula (I-5)

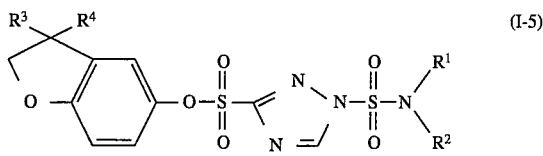

in which $R^1$, $R^2$, $R^3$ and $R^4$ are the same as in general formula (I).

(2) If l in general formula (I) is 0:

(vi) General formula (I-6)

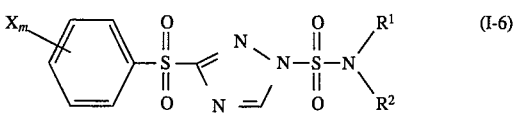

In which $R^1$, $R^2$, X and m are the same as in general formula (I).

(vii) General formula (I-7)

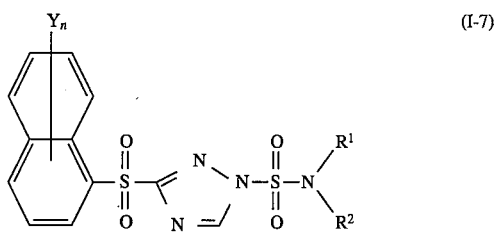

in which $R^1$, $R^2$, Y and n are the same as in general formula (I).

(viii) General formula (I-8)

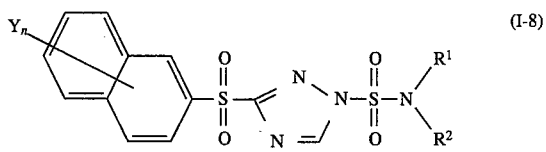

in which $R^1$, $R^2$, Y and n are the same as in general formula (I).

(ix) General formula (I-9)

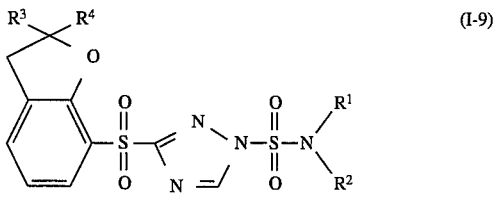

in which $R^1$, $R^2$, $R^3$ and $R^4$ are the same as In general formula (I).

(x) General formula (I-10)

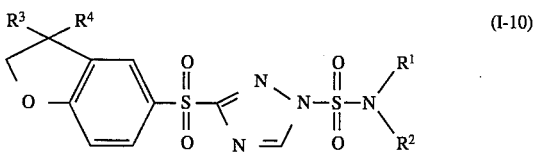

in which $R^1$, $R^2$, $R^3$ and $R^4$ are the same as in general formula (I).

(xi) General formula (I-11)

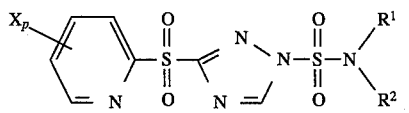

in which X, $R^1$, $R^2$ and p are the same as in general formula (I).

Examples of the compounds expressed by formula (I-1) according to the present invention are shown in Table 1, examples of the compounds expressed by formula (I-2) are shown in Table 2, examples of the compounds expressed by formula (I-3) are shown in Table 3, examples of the compounds expressed by formula (I-4) are shown in Table 4, examples of the compounds expressed by formula (I-5) are shown in Table 5, examples of the compounds expressed by formula (I-6) are shown in Table 6, examples of the compounds expressed by formula (I-7) are shown in Table 7, examples of the compounds expressed by formula (I-8) are shown in Table 8, examples of the compounds expressed by formula (I-9) are shown in Table 9, examples of the compounds expressed by formula (I-10) are shown in Table 10 and examples of the compounds expressed by formula (I-11) are shown in Table 11.

The abbreviations in Tables 1 to 11 respectively denote the following:

Me denotes a methyl group, Et denotes an ethyl group, nPr denotes an n-propyl group, iPr denotes an isopropyl group and tBu denotes a t-butyl group.

TABLE 1

| Compound No. | $R^1$ | $R^2$ | $X_m$ |
|---|---|---|---|
| 1 | Me | Me | H |
| 2 | Me | Et | H |
| 3 | Et | Et | H |
| 4 | Et | nPr | H |
| 5 | Et | iPr | H |
| 6 | nPr | nPr | H |
| 7 | —CH(Me)-(CH$_2$)$_3$—CH$_2$— | | H |
| 8 | —CH(Me)-(CH$_2$)$_3$—CH(Me)- | | H |
| 9 | —CH(Et)-(CH$_2$)$_3$—CH$_2$— | | H |
| 10 | Me | Me | 2-Me |
| 11 | Et | Et | 2-Me |
| 12 | Me | Me | 3-Me |
| 13 | Et | Et | 3-Me |
| 14 | Me | Me | 4-Me |
| 15 | Et | Et | 4-Me |
| 16 | —CH(Me)-(CH$_2$)$_3$—CH$_2$— | | 4-Me |
| 17 | Me | Me | 2-Et |
| 18 | Et | Et | 2-Et |
| 19 | Me | Me | 3-Et |
| 20 | Et | Et | 3-Et |
| 21 | Me | Me | 4-Et |
| 22 | Et | Et | 4-Et |
| 23 | Me | Me | 2-iPr |
| 24 | Et | Et | 2-iPr |
| 25 | Me | Me | 3-iPr |
| 26 | Et | Et | 3-iPr |
| 27 | Me | Me | 4-iPr |
| 28 | Et | Et | 4-iPr |
| 29 | Me | Me | 4-tBu |
| 30 | Et | Et | 4-tBu |
| 31 | Me | Me | 2-F |
| 32 | Et | Et | 2-F |
| 33 | Me | Me | 3-F |
| 34 | Et | Et | 3-F |
| 35 | Me | Me | 4-F |
| 36 | Et | Et | 4-F |
| 37 | Me | Me | 2-Cl |
| 38 | Et | Et | 2-Cl |
| 39 | Me | Me | 3-Cl |
| 40 | Et | Et | 3-Cl |
| 41 | Me | Me | 4-Cl |
| 42 | Et | Et | 4-Cl |
| 43 | Me | Me | 2-Br |
| 44 | Et | Et | 2-Br |
| 45 | Me | Me | 2-CH$_2$CH=CH$_2$ |
| 46 | Et | Et | 2-CH$_2$CH=CH$_2$ |
| 47 | Me | Me | 2-OMe |
| 48 | Et | Et | 2-OMe |
| 49 | Me | Me | 3-OMe |
| 50 | Et | Et | 3-OMe |
| 51 | Me | Me | 4-OMe |
| 52 | Et | Et | 4-OMe |
| 53 | Me | Me | 3-OEt |
| 54 | Et | Et | 3-OEt |
| 55 | Me | Me | 4-OEt |
| 56 | Et | Et | 4-OEt |
| 57 | Me | Me | 2-CF$_3$ |

TABLE 1-continued

| Compound No. | R¹ | R² | $X_m$ |
|---|---|---|---|
| 58 | Et | Et | 2-CF₃ |
| 59 | Me | Me | 3-CF₃ |
| 60 | Et | Et | 3-CF₃ |
| 61 | Me | Me | 4-CF₃ |
| 62 | Et | Et | 4-CF₃ |
| 63 | Me | Me | 2-OCHF₂ |
| 64 | Et | Et | 2-OCHF₂ |
| 65 | Me | Me | 4-OCHF₂ |
| 66 | Et | Et | 4-OCHF₂ |
| 67 | Me | Me | 2-OCH₂CF₃ |
| 68 | Et | Et | 2-OCH₂CF₃ |
| 69 | Me | Me | 4-OCH₂CF₃ |
| 70 | Et | Et | 4-OCH₂CF₃ |
| 71 | Me | Me | 2-OCF₂CFClH |
| 72 | Et | Et | 2-OCF₂CFClH |
| 73 | Me | Me | 2-C₆H₅ |
| 74 | Et | Et | 2-C₆H₅ |
| 75 | Me | Me | 2-CH₂C₆H₅ |
| 76 | Et | Et | 2-CH₂C₆H₅ |
| 77 | Me | Me | 2-OCH₂C₆H₅ |
| 78 | Et | Et | 2-OCH₂C₆H₅ |
| 79 | Me | Me | 2-COCH₃ |
| 80 | Et | Et | 2-COCH₃ |
| 81 | Me | Me | 2-COOMe |
| 82 | Et | Et | 2-COOMe |
| 83 | Me | Me | 4-COOMe |
| 84 | Et | Et | 4-COOMe |
| 85 | Me | Me | 2-CHO |
| 86 | Et | Et | 2-CHO |
| 87 | Me | Me | 2-NO₂ |
| 88 | Et | Et | 2-NO₂ |
| 89 | Me | Me | 4-NO₂ |
| 90 | Et | Et | 4-NO₂ |
| 91 | Me | Me | 2-CN |
| 92 | Et | Et | 2-CN |
| 93 | Me | Me | 3-CN |
| 94 | Et | Et | 3-CN |
| 95 | Me | Me | 4-CN |
| 96 | Et | Et | 4-CN |
| 97 | Me | Me | 2-NHCOCH₃ |
| 98 | Et | Et | 2-NHCOCH₃ |
| 99 | Me | Me | 4-NHCOCH₃ |
| 100 | Et | Et | 4-NHCOCH₃ |
| 101 | Me | Me | 2,6-(Me)₂ |
| 102 | Me | Et | 2,6-(Me)₂ |
| 103 | Et | Et | 2,6-(Me)₂ |
| 104 | Et | nPr | 2,6-(Me)₂ |
| 105 | Et | iPr | 2,6-(Me)₂ |
| 106 | nPr | nPr | 2,6-(Me)₂ |
| 107 | —CH(Me)-(CH₂)₃—CH₂— | | 2,6-(Me)₂ |
| 108 | Me | Me | 2,4-(Me)₂ |
| 109 | Et | Et | 2,4-(Me)₂ |
| 110 | Me | Me | 3,4-(Me)₂ |
| 111 | Et | Et | 3,4-(Me)₂ |
| 112 | Me | Me | 3,5-(Me)₂ |
| 113 | Et | Et | 3,5-(Me)₂ |
| 114 | Me | Me | 2,3-(Me)₂ |
| 115 | Et | Et | 2,3-(Me)₂ |
| 116 | Me | Me | 2,6-(Et)₂ |
| 117 | Et | Et | 2,6-(Et)₂ |
| 118 | Me | Me | 2-Me-6-Et |
| 119 | Et | Et | 2-Me-6-Et |
| 120 | Me | Me | 2-Me-5-iPr |
| 121 | Et | Et | 2-Me-5-iPr |
| 122 | Me | Me | 2-iPr-5-Me |
| 123 | Et | Et | 2-iPr-5-Me |
| 124 | Me | Me | 2-Me-4-Cl |
| 125 | Et | Et | 2-Me-4-Cl |
| 126 | Me | Me | 2-Me-6-Cl |
| 127 | Et | Et | 2-Me-6-Cl |
| 128 | Me | Me | 3-Me-4-Cl |
| 129 | Et | Et | 3-Me-4-Cl |
| 130 | Me | Me | 2-Me-4-F |
| 131 | Et | Et | 2-Me-4-F |
| 132 | Me | Mer | 2,4-F₂ |
| 133 | Et | Etr | 2,4-F₂ |

TABLE 1-continued

| Compound No. | $R^1$ | $R^2$ | $X_m$ |
|---|---|---|---|
| 134 | Me | Me | 2,6-$F_2$ |
| 135 | Et | Et | 2,6-$F_2$ |
| 136 | Me | Me | 2,3-$Cl_2$ |
| 137 | Et | Et | 2,3-$Cl_2$ |
| 138 | Me | Me | 2,4-$Cl_2$ |
| 139 | Et | Et | 2,4-$Cl_2$ |
| 140 | Me | Me | 2,5-$Cl_2$ |
| 141 | Et | Et | 2,5-$Cl_2$ |
| 142 | Me | Me | 2,6-$Cl_2$ |
| 143 | Et | Et | 2,6-$Cl_2$ |
| 144 | Me | Me | 2-Cl-4-F |
| 145 | Et | Et | 2-Cl-4-F |
| 146 | Me | Me | 2-Cl-6-F |
| 147 | Et | Et | 2-Cl-6-F |
| 148 | Me | Me | 4-Cl-2-F |
| 139 | Et | Et | 4-Cl-2-F |
| 150 | Me | Me | 2-OMe-4-Me |
| 151 | Et | Et | 2-OMe-4-Me |
| 152 | Me | Me | 2,6-$(OMe)_2$ |
| 153 | Et | Et | 2,6-$(OMe)_2$ |
| 154 | Me | Me | 2-F-6-OMe |
| 155 | Et | Et | 2-F-6-OMe |
| 156 | Me | Me | 3-Cl-5-OMe |
| 157 | Et | Et | 3-Cl-5-OMe |
| 158 | Me | Me | 2-OMe-4-CH=$CHCH_3$ |
| 159 | Et | Et | 2-OMe-4-CH=$CHCH_3$ |
| 160 | Me | m | 2-OMe-4-$CH_2$CH=$CH_2$ |
| 161 | Et | Et | 2-OMe-4-$CH_2$CH=$CH_2$ |
| 162 | Me | Me | 3,5-$(CF_3)_2$ |
| 163 | Et | Et | 3,5-$(CF_3)_2$ |
| 164 | Me | Me | 2-Cl-4-$CF_3$ |
| 165 | Et | Et | 2-Cl-4-$CF_3$ |
| 166 | Me | Me | 2-Cl-5-$CF_3$ |
| 167 | Et | Et | 2-Cl-5-$CF_3$ |
| 168 | Me | Me | 2-Me-6-COOMe |
| 169 | Et | Et | 2-Me-6-COOMe |
| 170 | Me | Me | 2-OMe-6-COOMe |
| 171 | Et | Et | 2-OMe-6-COOMe |
| 172 | Me | Me | 2-Cl-6-COOMe |
| 173 | Et | Et | 2-Cl-6-COOMe |
| 174 | Me | Me | 2-$NO_2$-3-Me |
| 175 | Et | Et | 2-$NO_2$-3-Me |
| 176 | Me | Me | 2-CN-4-F |
| 177 | Et | Et | 2-CN-4-F |
| 178 | Me | Me | 2-CN-4-Cl |
| 179 | Et | Et | 2-CN-4-Cl |
| 180 | Me | Me | 2-CN-4-Br |
| 181 | Et | Et | 2-CN-4-Br |
| 182 | Me | Me | 4-CN-2-F |
| 183 | Et | Et | 4-CN-2-F |
| 184 | Me | Me | 4-CN-2-Cl |
| 185 | Et | Et | 4-CN-2-Cl |
| 186 | Me | Me | 4-CN-2-Br |
| 187 | Et | Et | 4-CN-2-Br |
| 188 | Me | Me | 2,3,5-$(Me)_3$ |
| 189 | Et | Et | 2,3,5-$(Me)_3$ |
| 190 | Me | Me | 2,3,6-$(Me)_3$ |
| 191 | Et | Et | 2,3,6-$(Me)_3$ |
| 192 | Me | Me | 2,4,6-$(Me)_3$ |
| 193 | Me | Et | 2,4,6-$(Me)_3$ |
| 194 | Et | Et | 2,4,6-$(Me)_3$ |
| 195 | Et | nPr | 2,4,6-$(Me)_3$ |
| 196 | Et | iPr | 2,4,6-$(Me)_3$ |
| 197 | nPr | nPr | 2,4,6-$(Me)_3$ |
| 198 | Me | Me | 2,4-$(Me)_2$-6-Cl |
| 199 | Et | Et | 2,4-$(Me)_2$-6-Cl |
| 200 | Me | Me | 2,6-$(Me)_2$-4-Cl |
| 201 | Et | Et | 2,6-$(Me)_2$-4-Cl |
| 202 | Me | Me | 2,4-$Cl_2$-6-Me |
| 203 | Et | Et | 2,4-$Cl_2$-6-Me |
| 204 | Me | Me | 2,6-$Cl_2$-4-Me |
| 205 | Et | Et | 2,6-$Cl_2$-4-Me |
| 206 | Me | Me | 2,4-$Cl_2$-3-Me |
| 207 | Et | Et | 2,4-$Cl_2$-3-Me |
| 208 | Me | Me | 2,6-$Cl_2$-4-$CF_3$ |
| 209 | Et | Et | 2,6-$Cl_2$-4-$CF_3$ |

TABLE 1-continued

| Compound No. | $R^1$ | $R^2$ | $X_m$ |
|---|---|---|---|
| 210 | Me | Me | 2,3,4-$Cl_3$ |
| 211 | Et | Et | 2,3,4-$Cl_3$ |
| 212 | Me | Me | 2,3,6-$Cl_3$ |
| 213 | Et | Et | 2,3,6-$Cl_3$ |
| 214 | Me | Me | 2,4,5-$Cl_3$ |
| 215 | Et | Et | 2,4,5-$Cl_3$ |
| 216 | Me | Me | 2,4,6-$Cl_3$ |
| 217 | Me | Et | 2,4,6-$Cl_3$ |
| 218 | Et | Et | 2,4,6-$Cl_3$ |
| 219 | Et | nPr | 2,4,6-$Cl_3$ |
| 220 | Et | iPr | 2,4,6-$Cl_3$ |
| 221 | nPr | nPr | 2,4,6-$Cl_3$ |
| 222 | Me | Me | 3,4,5-$(OMe)_3$ |
| 223 | Et | Et | 3,4,5-$(OMe)_3$ |
| 224 | Me | Me | 2,4-$Cl_2$-6-COOMe |
| 225 | Et | Et | 2,4-$Cl_2$-6-COOMe |
| 226 | Me | Me | 2-$NO_2$-3,5-$(Me)_2$ |
| 227 | Et | Et | 2-$NO_2$-3,5-$(Me)_2$ |
| 228 | Me | Me | 2,3,5,6-$F_4$ |
| 229 | Et | Et | 2,3,5,6-$F_4$ |
| 230 | Me | Me | 2,3,4,5,6-$F_5$ |
| 231 | Et | Et | 2,3,4,5,6-$F_5$ |
| 232 | Me | Me | 2,3,4,5,6-$Cl_5$ |
| 233 | Et | Et | 2,3,4,5,6-$Cl_5$ |
| 234 | Me | Me | 2,3,4,5,6-$(Me)_5$ |
| 235 | Et | Et | 2,3,4,5,6-$(Me)_5$ |

TABLE 2

| Compound No. | $R^1$ | $R^2$ | $Y_n$ |
|---|---|---|---|
| 236 | Me | Me | H |
| 237 | Et | Et | H |
| 238 | Me | Me | 4-Cl |
| 239 | Et | Et | 4-Cl |
| 240 | Me | Me | 2-Me |
| 241 | Et | Et | 2-Me |
| 242 | Me | Me | 2-OMe |
| 243 | Et | Et | 2-OMe |
| 244 | Me | Me | 4-$CF_3$ |
| 245 | Et | Et | 4-$CF_3$ |
| 246 | Me | Me | 2-$OCH_2CF_3$ |
| 247 | Et | Et | 2-$OCH_2CF_3$ |
| 248 | Me | Me | 2-$COCH_3$ |
| 249 | Et | Et | 2-$COCH_3$ |
| 250 | Me | Me | 2-CHO |
| 251 | Et | Et | 2-CHO |
| 252 | Me | Me | 2-COOMe |
| 253 | Et | Et | 2-COOMe |
| 254 | Me | Me | 2-$NO_2$ |
| 255 | Et | Et | 2-$NO_2$ |
| 256 | Me | Me | 4-$NHCOCH_3$ |
| 257 | Et | Et | 4-$NHCOCH_3$ |

TABLE 3

| Compound No. | $R^1$ | $R^2$ | $Y_n$ |
|---|---|---|---|
| 258 | Me | Me | H |
| 259 | Et | Et | H |
| 260 | Me | Me | 1-Br |
| 261 | Et | Et | 1-Br |
| 262 | Me | Me | 1-Me |
| 263 | Et | Et | 1-Me |
| 264 | Me | Me | 1-OMe |
| 265 | Et | Et | 1-OMe |
| 266 | Me | Me | 1-$CF_3$ |
| 267 | Et | Et | 1-$CF_3$ |
| 268 | Me | Me | 1-$OCH_2CF_3$ |
| 269 | Et | Et | 1-$OCH_2CF_3$ |
| 270 | Me | Me | 1-$COCH_3$ |
| 271 | Et | Et | 1-$COCH_3$ |
| 272 | Me | Me | 1-CHO |
| 273 | Et | Et | 1-CHO |
| 274 | Me | Me | 3-COOMe |
| 275 | Et | Et | 3-COOMe |
| 276 | Me | Me | 1-$NO_2$ |
| 277 | Et | Et | 1-$NO_2$ |
| 278 | Me | Me | 3-$NHCOCH_3$ |
| 279 | Et | Et | 3-$NHCOCH_3$ |

TABLE 4

| Compound No. | $R^1$ | $R^2$ | $R^3$ | $R^4$ |
|---|---|---|---|---|
| 280 | Me | Me | H | H |
| 281 | Et | Et | H | H |
| 282 | Me | Me | Me | H |
| 283 | Et | Et | Me | H |
| 284 | Me | Me | Me | Me |
| 285 | Me | Et | Me | Me |
| 286 | Et | Et | Me | Me |
| 287 | Et | nPr | Me | Me |
| 288 | Et | iPr | Me | Me |
| 289 | nPr | nPr | Me | Me |

TABLE 5

| Compound No. | $R^1$ | $R^2$ | $R^3$ | $R^4$ |
|---|---|---|---|---|
| 290 | Me | Me | H | H |
| 291 | Et | Et | H | H |
| 292 | Me | Me | Me | H |
| 293 | Et | Et | Me | H |
| 294 | Me | Me | Me | Me |

TABLE 5-continued

| Compound No. | $R^1$ | $R^2$ | $R^3$ | $R^4$ |
|---|---|---|---|---|
| 295 | Me | Et | Me | Me |
| 296 | Et | Et | Me | Me |
| 297 | Et | nPr | Me | Me |

TABLE 5-continued

| Compound No. | $R^1$ | $R^2$ | $R^3$ | $R^4$ |
|---|---|---|---|---|
| 298 | Et | iPr | Me | Me |
| 299 | nPr | nPr | Me | Me |

TABLE 6

| Compound No. | $R^1$ | $R^2$ | $X_m$ |
|---|---|---|---|
| 301 | Me | Me | H |
| 302 | Me | Et | H |
| 303 | Et | Et | H |
| 304 | Et | nPr | H |
| 305 | Et | iPr | H |
| 306 | nPr | nPr | H |
| 307 | —CH(Me)-(CH$_2$)$_3$—CH$_2$— | | H |
| 308 | —CH(Me)-(CH$_2$)$_3$—CH(Me)- | | H |
| 309 | —CH(Et)-(CH$_2$)$_3$—CH$_2$— | | H |
| 310 | Me | Me | 2-Me |
| 311 | Et | Et | 2-Me |
| 312 | Me | Me | 3-Me |
| 313 | Et | Et | 3-Me |
| 314 | Me | Me | 4-Me |
| 315 | Et | Et | 4-Me |
| 316 | —CH(Me)-(CH$_2$)$_3$—CH$_2$— | | 4-Me |
| 317 | Me | Me | 2-Et |
| 318 | Et | Et | 2-Et |
| 319 | Me | Me | 3-Et |
| 320 | Et | Et | 3-Et |
| 321 | Me | Me | 4-Et |
| 322 | Et | Et | 4-Et |
| 323 | Me | Me | 2-iPr |
| 324 | Et | Et | 2-iPr |
| 325 | Me | Me | 3-iPr |
| 326 | Et | Et | 3-iPr |
| 327 | Me | Me | 4-iPr |
| 328 | Et | Et | 4-iPr |
| 329 | Me | Me | 4-tBu |
| 330 | Et | Et | 4-tBu |
| 331 | Me | Me | 2-F |
| 332 | Et | Et | 2-F |
| 333 | Me | Me | 3-F |
| 334 | Et | Et | 3-F |
| 335 | Me | Me | 4-F |
| 336 | Et | Et | 4-F |
| 337 | Me | Me | 2-Cl |
| 338 | Et | Et | 2-Cl |
| 339 | Me | Me | 3-Cl |
| 340 | Et | Et | 3-Cl |
| 341 | Me | Me | 4-Cl |
| 342 | Et | Et | 4-Cl |
| 343 | Me | Me | 2-Br |
| 344 | Et | Et | 2-Br |
| 345 | Me | Me | 2-CH$_2$CH=CH$_2$ |
| 346 | Et | Et | 2-CH$_2$CH=CH$_2$ |
| 347 | Me | Me | 2-OMe |
| 348 | Et | Et | 2-OMe |
| 349 | Me | Me | 3-OMe |
| 350 | Et | Et | 3-OMe |
| 351 | Me | Me | 4-OMe |
| 352 | Et | Et | 4-OMe |
| 353 | Me | Me | 3-OEt |
| 354 | Et | Et | 3-OEt |
| 355 | Me | Me | 4-OEt |
| 356 | Et | Et | 4-OEt |
| 357 | Me | Me | 2-CF |
| 358 | Et | Et | 2-CF$_3$ |
| 359 | Me | Me | 3-CF$_3$ |
| 360 | Et | Et | 3-CF$_3$ |
| 361 | Me | Me | 4-CF$_3$ |
| 362 | Et | Et | 4-CF$_3$ |
| 363 | Me | Me | 2-OCHF$_2$ |
| 364 | Et | Et | 2-OCHF$_2$ |
| 365 | Me | Me | 4-OCHF$_2$ |

TABLE 6-continued

| Compound No. | R¹ | R² | X_m |
|---|---|---|---|
| 366 | Et | Et | 4-OCHF$_2$ |
| 367 | Me | Me | 2-OCH$_2$CF$_3$ |
| 368 | Et | Et | 2-OCH$_2$CF$_3$ |
| 369 | Me | Me | 4-OCH$_2$CF$_3$ |
| 370 | Et | Et | 4-OCH$_2$CF$_3$ |
| 371 | Me | Me | 2-OCF$_2$CFClH |
| 372 | Et | Et | 2-OCF$_2$CFClH |
| 373 | Me | Me | 2-C$_6$H$_5$ |
| 374 | Et | Et | 2-C$_6$H$_5$ |
| 375 | Me | Me | 2-CH$_2$C$_6$H$_5$ |
| 376 | Et | Et | 2-CH$_2$C$_6$H$_5$ |
| 377 | Me | Me | 2-OCH$_2$C$_6$H$_5$ |
| 378 | Et | Et | 2-OCH$_2$C$_6$H$_5$ |
| 379 | Me | Me | 2-COCH$_3$ |
| 380 | Et | Et | 2-COCH$_3$ |
| 381 | Me | Me | 2-COOMe |
| 382 | Et | Et | 2-COOMe |
| 383 | Me | Me | 4-COOMe |
| 384 | Et | Et | 4-COOMe |
| 385 | Me | Me | 2-CHO |
| 386 | Et | Et | 2-CHO |
| 387 | Me | Me | 2-NO$_2$ |
| 388 | Et | Et | 2-NO$_2$ |
| 389 | Me | Me | 4-NO$_2$ |
| 390 | Et | Et | 4-NO$_2$ |
| 391 | Me | Me | 2-CN |
| 392 | Et | Et | 2-CN |
| 393 | Me | Me | 3-CN |
| 394 | Et | Et | 3-CN |
| 395 | Me | Me | 4-CN |
| 396 | Et | Et | 4-CN |
| 397 | Me | Me | 2-NHCOCH$_3$ |
| 398 | Et | Et | 2-NHCOCH$_3$ |
| 399 | Me | Me | 4-NHCOCH$_3$ |
| 400 | Et | Et | 4-NHCOCH$_3$ |
| 401 | Me | Me | 2,6-(Me)$_2$ |
| 402 | Me | Et | 2,6-(Me)$_2$ |
| 403 | Et | Et | 2,6-(Me)$_2$ |
| 404 | Et | nPr | 2,6-(Me)$_2$ |
| 405 | Et | iPr | 2,6-(Me)$_2$ |
| 406 | nPr | nPr | 2,6-(Me)$_2$ |
| 407 | —CH(Me)-(CH$_2$)$_3$—CH$_2$— | | 2,6-(Me)$_2$ |
| 408 | Me | Me | 2,4-(Me)$_2$ |
| 409 | Et | Et | 2,4-(Me)$_2$ |
| 410 | Me | Me | 3,4-(Me)$_2$ |
| 411 | Et | Et | 4-(Me)$_2$ |
| 412 | Me | Me | 3,5-(Me)$_2$ |
| 413 | Et | Et | 3,5-(Me)$_2$ |
| 414 | Me | Me | 2,3-(Me)$_2$ |
| 415 | Et | Et | 2,3-(Me)$_2$ |
| 416 | Me | Me | 2,6-(Et)$_2$ |
| 417 | Et | Et | 2,6-(Et)$_2$ |
| 418 | Me | Me | 2-Me-6-Et |
| 419 | Et | Et | 2-Me-6-Et |
| 420 | Me | Me | 2-Me-5-iPr |
| 421 | Et | Et | 2-Me-5-iPr |
| 422 | Me | Me | 2-iPr-5-Me |
| 423 | Et | Et | 2-iPr-5-Me |
| 424 | Me | Me | 2-Me-4-Cl |
| 425 | Et | Et | 2-Me-4-Cl |
| 426 | Me | Me | 2-Me-6-Cl |
| 427 | Et | Et | 2-Me-6-Cl |
| 428 | Me | Me | 3-Me-4-Cl |
| 429 | Et | Et | 3-Me-4-Cl |
| 430 | Me | Me | 2-Me-4-F |
| 431 | Et | Et | 2-Me-4-F |
| 432 | Me | Me | 2,4-F$_2$ |
| 433 | Et | Etr | 2,4-F$_2$ |
| 434 | Me | Me | 2,6-F$_2$ |
| 435 | Et | Et | 2,6-F$_2$ |
| 436 | Me | Me | 2,3-Cl$_2$ |
| 437 | Et | Et | 2,3-Cl$_2$ |
| 438 | Me | Me | 2,4-Cl$_2$ |
| 439 | Et | Et | 2,4-Cl$_2$ |
| 440 | Me | Me | 2,5-Cl$_2$ |
| 441 | Et | Et | 2,5-Cl$_2$ |

TABLE 6-continued

| Compound No. | $R^1$ | $R^2$ | $X_m$ |
|---|---|---|---|
| 442 | Me | Me | 2,6-Cl$_2$ |
| 443 | Et | Et | 2,6-Cl$_2$ |
| 444 | Me | Me | 2-Cl-4-F |
| 445 | Et | Et | 2-Cl-4-F |
| 446 | Me | Me | 2-Cl-6-F |
| 447 | Et | Et | 2-Cl-6-F |
| 448 | Me | Me | 4-Cl-2-F |
| 449 | Et | Et | 4-Cl-2-F |
| 450 | Me | Me | 2-OMe-4-Me |
| 451 | Et | Et | 2-OMe-4-Me |
| 452 | Me | Me | 2,6-(OMe)$_2$ |
| 453 | Et | Et | 2,6-(OMe)$_2$ |
| 454 | Me | Me | 2-F-6-OMe |
| 455 | Et | Et | 2-F-6-OMe |
| 456 | Me | Me | 3-Cl-5-OMe |
| 457 | Et | Et | 3-Cl-5-OMe |
| 458 | Me | Me | 2-OMe-4-CH=CHCH$_3$ |
| 459 | Et | Et | 2-OMe-4-CH=CHCH$_3$ |
| 460 | Me | Me | 2-OMe-4-CH$_2$CH=CH$_2$ |
| 461 | Et | Et | 2-OMe-4-CH$_2$CH=CH$_2$ |
| 462 | Me | Me | 3,5-(CF$_3$)$_2$ |
| 463 | Et | Et | 3,5-(CF$_3$)$_2$ |
| 464 | Me | Me | 2-Cl-4-CF$_3$ |
| 465 | Et | Et | 2-Cl-4-CF$_3$ |
| 466 | Me | Me | 2-Cl-5-CF$_3$ |
| 467 | Et | Et | 2-Cl-5-CF$_3$ |
| 468 | Me | Me | 2-Me-6-COOMe |
| 469 | Et | Et | 2-Me-6-COOMe |
| 470 | Me | Me | 2-OMe-6-COOMe |
| 471 | Et | Et | 2-OMe-6-COOMe |
| 472 | Me | Me | 2-Cl-6-COOMe |
| 473 | Et | Et | 2-Cl-6-COOMe |
| 474 | Me | Me | 2-NO$_2$-3-Me |
| 475 | Et | Et | 2-NO$_2$-3-Me |
| 476 | Me | Me | 2-CN-4-F |
| 477 | Et | Et | 2-CN-4-F |
| 478 | Me | Me | 2-CN-4-Cl |
| 479 | Et | Et | 2-CN-4-Cl |
| 480 | Me | Me | 2-CN-4-Br |
| 481 | Et | Et | 2-CN-4-Br |
| 482 | Me | Me | 4-CN-2-F |
| 483 | Et | Et | 4-CN-2-F |
| 484 | Me | Me | 4-CN-2-Cl |
| 485 | Et | Et | 4-CN-2-Cl |
| 486 | Me | Me | 4-CN-2-Br |
| 487 | Et | Et | 4-CN-2-Br |
| 488 | Me | Me | 2,3,5-(Me)$_3$ |
| 489 | Et | Et | 2,3,5-(Me)$_3$ |
| 490 | Me | Me | 2,3,6-(Me)$_3$ |
| 491 | Et | Et | 2,3,6-(Me)$_3$ |
| 492 | Me | Me | 2,4,6-(Me)$_3$ |
| 493 | Me | Et | 2,4,6-(Me)$_3$ |
| 494 | Et | Et | 2,4,6-(Me)$_3$ |
| 495 | Et | nPr | 2,4,6-(Me)$_3$ |
| 496 | Et | iPr | 2,4,6-(Me)$_3$ |
| 497 | nPr | nPr | 2,4,6-(Me)$_3$ |
| 498 | Me | Me | 2,4-(Me)$_2$-6-Cl |
| 499 | Et | Et | 2,4-(Me)$_2$-6-Cl |
| 500 | Me | Me | 2,6-(Me)$_2$-4-Cl |
| 501 | Et | Et | 2,6-(Me)$_2$-4-Cl |
| 502 | Me | Me | 2,4-Cl$_2$-6-Me |
| 503 | Et | Et | 2,4-Cl$_2$-6-Me |
| 504 | Me | Me | 2,6-Cl$_2$-4-Me |
| 505 | Et | Et | 2,6-Cl$_2$-4-Me |
| 506 | Me | Me | 2,4-Cl$_2$-3-Me |
| 507 | Et | Et | 2,4-Cl$_2$-3-Me |
| 508 | Me | Me | 2,6-Cl$_2$-4-CF$_3$ |
| 509 | Et | Et | 2,6-Cl$_2$-4-CF$_3$ |
| 510 | Me | Me | 2,3,4-Cl$_3$ |
| 511 | Et | Et | 2,3,4-Cl$_3$ |
| 512 | Me | Me | 2,3,6-Cl$_3$ |
| 513 | Et | Et | 2,3,6-Cl$_3$ |
| 514 | Me | Me | 2,4,5-Cl$_3$ |
| 515 | Et | Et | 2,4,5-Cl$_3$ |
| 516 | Me | Me | 2,4,6-Cl$_3$ |
| 517 | Me | Et | 2,4,6-Cl$_3$ |

TABLE 6-continued

| Compound No. | R¹ | R² | $X_m$ |
|---|---|---|---|
| 518 | Et | Et | 2,4,6-Cl₃ |
| 519 | Et | nPr | 2,4,6-Cl₃ |
| 520 | Et | iPr | 2,4,6-Cl₃ |
| 521 | nPr | nPr | 2,4,6-Cl₃ |
| 522 | Me | Me | 3,4,5-(OMe)₃ |
| 523 | Et | Et | 3,4,5-(OMe)₃ |
| 524 | Me | Me | 2,4-Cl₂-6-COOMe |
| 525 | Et | Et | 2,4-Cl₂-6-COOMe |
| 526 | Me | Me | 2-NO₂-3,5-(Me)₂ |
| 527 | Et | Et | 2-NO₂-3,5-(Me)₂ |
| 528 | Me | Me | 2,3,5,6-F₄ |
| 529 | Et | Et | 2,3,5,6-F₄ |
| 530 | Me | Me | 2,3,4,5,6-F₅ |
| 531 | Et | Et | 2,3,4,5,6-F₅ |
| 532 | Me | Me | 2,3,4,5,6-Cl₅ |
| 533 | Et | Et | 2,3,4,5,6-Cl₅ |
| 534 | Me | Me | 2,3,4,5,6-(Me)₅ |
| 535 | Et | Et | 2,3,4,5,6-(Me)₅ |

TABLE 7

| Compound No. | R¹ | R² | $Y_n$ |
|---|---|---|---|
| 536 | Me | Me | H |
| 537 | Et | Et | H |
| 538 | Me | Me | 4-Cl |
| 539 | Et | Et | 4-Cl |
| 540 | Me | Me | 2-Me |
| 541 | Et | Et | 2-Me |
| 542 | Me | Me | 2-OMe |
| 543 | Et | Et | 2-OMe |
| 544 | Me | Me | 4-CF₃ |
| 545 | Et | Et | 4-CF₃ |
| 546 | Me | Me | 2-OCH₂CF₃ |
| 547 | Et | Et | 2-OCH₂CF₃ |
| 548 | Me | Me | 2-COCH₃ |
| 549 | Et | Et | 2-COCH₃ |
| 550 | Me | Me | 2-CHO |
| 551 | Et | Et | 2-CHO |
| 552 | Me | Me | 2-COOMe |
| 553 | Et | Et | 2-COOMe |
| 554 | Me | Me | 2-NO₂ |
| 555 | Et | Et | 2-NO₂ |
| 556 | Me | Me | 4-NHCOCH₃ |
| 557 | Et | Et | 4-NHCOCH₃ |

TABLE 8

| Compound No. | R¹ | R² | $Y_n$ |
|---|---|---|---|
| 558 | Me | Me | H |
| 559 | Et | Et | H |
| 560 | Me | Me | 1-Br |
| 561 | Et | Et | 1-Br |
| 562 | Me | Me | 1-Me |
| 563 | Et | Et | 1-Me |
| 564 | Me | Me | 1-OMe |
| 565 | Et | Et | 1-OMe |
| 566 | Me | Me | 1-CF₃ |
| 567 | Et | Et | 1-CF₃ |
| 568 | Me | Me | 1-OCH₂CF₃ |
| 569 | Et | Et | 1-OCH₂CF₃ |
| 570 | Me | Me | 1-COCH₃ |
| 571 | Et | Et | 1-COCH₃ |
| 572 | Me | Me | 1-CHO |
| 573 | Et | Et | 1-CHO |
| 574 | Me | Me | 3-COOMe |
| 575 | Et | Et | 3-COOMe |
| 576 | Me | Me | 1-NO₂ |
| 577 | Et | Et | 1-NO₂ |
| 578 | Me | Me | 3-NHCOCH₃ |
| 579 | Et | Et | 3-NHCOCH₃ |

TABLE 9

| Compound No. | R¹ | R² | R³ | R⁴ |
|---|---|---|---|---|
| 580 | Me | Me | H | H |
| 581 | Et | Et | H | H |
| 582 | Me | Me | Me | H |
| 583 | Et | Et | Me | H |
| 584 | Me | Me | Me | Me |
| 585 | Me | Et | Me | Me |
| 586 | Et | Et | Me | Me |
| 587 | Et | nPr | Me | Me |
| 588 | Et | iPr | Me | Me |
| 589 | nPr | nPr | Me | Me |

TABLE 10

| Compound No. | R¹ | R² | R³ | R⁴ |
|---|---|---|---|---|
| 590 | Me | Me | H | H |
| 591 | Et | Et | H | H |
| 592 | Me | Me | Me | H |
| 593 | Et | Et | Me | H |
| 594 | Me | Me | Me | Me |
| 595 | Me | Et | Me | Me |
| 596 | Et | Et | Me | Me |
| 597 | Et | nPr | Me | Me |
| 598 | Et | iPr | Me | Me |
| 599 | nPr | nPr | Me | Me |

TABLE 11

| Compounds No. | R¹ | R² | $X_p$ |
|---|---|---|---|
| 600 | Me | Me | 3-CF₃ |
| 601 | Et | Et | 3-CF₃ |
| 602 | Me | Me | 4-CF₃ |

TABLE 11-continued

| Compounds No. | R¹ | R² | $X_p$ |
|---|---|---|---|
| 603 | Et | Et | 4-CF₃ |
| 604 | Me | Me | 5-CF₃ |
| 605 | Et | Et | 5-CF₃ |
| 606 | Me | Me | 6-CF₃ |
| 607 | Et | Et | 6-CF₃ |
| 608 | Me | Me | 3-Cl-4-CF₃ |
| 609 | Et | Et | 3-Cl-4-CF₃ |
| 610 | Me | Me | 3-Cl-5-CF₃ |
| 611 | Et | Et | 3-Cl-5-CF₃ |
| 612 | Me | Me | 3-Cl-6-CF₃ |
| 613 | Et | Et | 3-Cl-6-CF₃ |

A method of manufacturing the compound according to the present invention and expressed by general formula (I) will now be described. However, the compounds according to the present invention is not limited to those manufactured by the following methods.

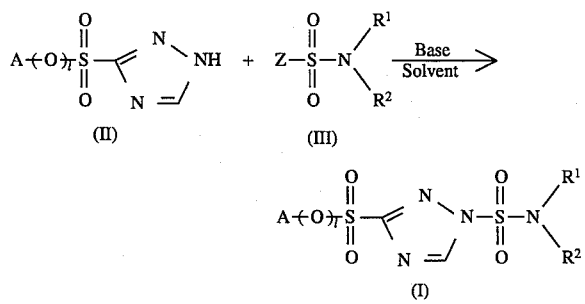

in which Z is a halogen atom, and A, l, R¹ and R² are the same as in general formula (I).

The compounds according to the present invention and expressed by general formula (I) can be obtained by causing a triazole derivatives expressed by general formula (II) and sulfamoylhalide expressed by general formula (III) to react with each other, preferably in a solvent, in the presence of a base. Although the quantities of the materials are not particularly limited, it is preferable that sulfamoylhalide (III) be 1 to 1.5 equivalents and the base be 1 to 5 equivalents with respect to 1 equivalent of triazole derivative (II).

The reaction temperature may be arbitrarily determined so far as it ranges from the temperature realized by ice cooling to the boiling point of the solvent.

Although the reaction time varies depending upon the conditions, the reactions can usually be completed in 10 minutes to 24 hours.

The solvent may be any one of the following materials selected from the group consisting of aliphatic hydrocarbons such as hexane, heptane, ligroin or petroleum ether; aromatic hydrocarbons such as benzene, toluene or xylene; halogenated hydrocarbons such as chloroform, carbon tetrachloride, dichloroethane, chlorobenzene or dichlorobenzene; ethers such as diethyl ether, diisopropyl ether, dioxane, tetrahydrofuran or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutylonitrile; tertiary amines such as pyridine, triethylamine, N,N-diethylaniline, tributylamine or N-methylmorpholine; acid amides such as N,N-dimethylformamide; and sulfur compounds such as dimethyl sulfoxide or sulforan; and their mixtures.

Examples of a base include organic bases such as pyridine, triethylamine or N,N-dietylaniline; inorganic bases such as sodium hydroxide, potassium hydroxide, sodium carbonate, potassium carbonate or sodium hydride; and alkali metal alkoxides such as sodium methoxide or sodium ethoxide.

Water is added to the solution, in which the reactions have been allowed to take place, and then subjected to normal post-processes such as extraction of the organic solvent, immersion, and the like. If necessary, the products may be purified by recrystallization, silica gel column chromatography or medium-pressure liquid chromatography.

The triazole derivatives expressed by general formula (II) can be manufactured by the following method (1) or (2). However, the triazole derivatives are not limited to that manufactured by the following methods.

(1) If l of the foregoing general formula is 1,

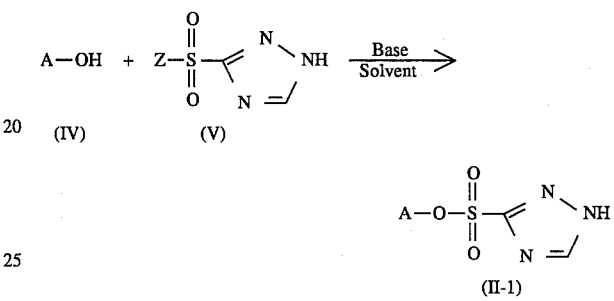

in which Z is a halogen atom and A is the same as in general formula (I).

The compounds expressed by general formula (II-1) can be obtained by causing the compounds expressed by general formula (IV) and the compounds expressed by general formula (V) to react with each other in an adequate solvent in the presence of a basic substance. Although the quantities of the materials are not particularly limited, the compound (V) Is preferably 1 to 1.2 equivalents with respect to 1 equivalent of the compound (IV).

The reaction temperature may be arbitrarily determined so far as it ranges from a level realized by ice-cooling to the boiling point of the solvent.

Although the reaction time varies depending upon the conditions, the reactions can usually be completed in 1 hour to 24 hours.

The solvent may be any of the following materials selected from a group consisting of aliphatic hydrocarbons such as hexane, heptane, ligroin or petroleum ether; aromatic hydrocarbons such as benzene, toluene or xylene; halogenated hydrocarbons such as chloroform, carbon tetrachloride, dichloroethane, chlorobenzene or dichlorobenzene; ethers such as diethyl ether, diisopropyl ether, dioxane, tetrahydrofuran or diethylene glycol dimethyl ether; ketones such as acetone, methyl ethyl ketone, methylisobutyl ketone, isophorone or cyclohexanone; nitro compounds such as nitroethane or nitrobenzene; nitriles such as acetonitrile or isobutylonitrile; tertiary amines such as pyridine, triethylamine, N,N-diethylaniline, tributyl amine or N-methylmorpholine; acid amides such as N,N-dimethylformamide; and sulfur compounds such as dimethyl sulfoxide or sulforan; and their mixtures.

Examples of a base include organic bases such as pyridine, triethylamine or N,N-dietylanitine; inorganic bases such as sodium hydroxide, potassium hydroxide, sodium carbonate, potassium carbonate or sodium hydride; and alkali metal alkoxides such as sodium methoxide or sodium ethoxide.

The products (II-1) can be isolated from the mixture of reactants by a usual method and can easily be purified by recrystallization or column chromatography.

(2) If 1 of the foregoing general formula is 0, the triazole derivatives expressed by general formula (II-2) can be manufactured by the following method A or B.

Method A

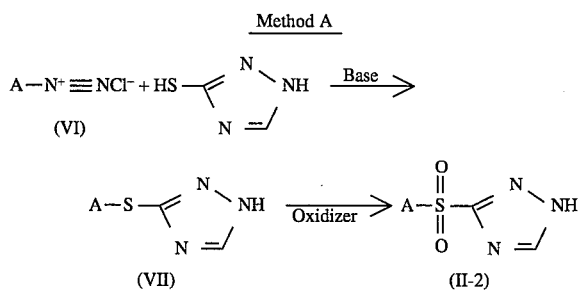

in which A is the same as in general formula (I).

The compounds expressed by general formula (VII) can be obtained by causing the compounds expressed by general formula (VI) and 3-mercapto-1,2,4-triazole to react with each other in an adequate solvent in the presence of a basic substance. Although the quantities of the materials are not particularly limited, 3-mercapto-1,2,4-triazole Is preferably 1 to 1.2 equivalents with respect to 1 equivalent of the compound (VI).

The reaction temperature may be arbitrarily determined so far as it ranges from −20° C. to 100° C.

Although the reaction time varies depending upon the conditions, the reactions can usually be completed in 1 hour to 24 hours.

The basic material may be an inorganic material such as alkaline carbonate or caustic alkali. Although the quantity of the basic material is not particularly limited, the basic material is preferably 1 to 1.5 equivalents with respect to 1 equivalent of the compound (VI).

The products (VII) can be isolated from the mixture of reactants by a usual method and can easily be purified by recrystallization or column chromatography.

The compounds expressed by general formula (II-2) can be obtained by causing the compounds expressed by general formula (VII) to react in an adequate solvent in the presence of an oxidant. Although the quantities of the materials are not particularly limited, the oxidant is preferably 2 to 5 equivalent with respect to 1 equivalent of the compound (VII).

The reaction temperature may be arbitrarily determined so far as it ranges from room temperature to 100° C. Although the reaction time varies depending upon the conditions, the reactions can usually be completed in 30 minutes to 24 hours.

Examples of solvent include: ketones such as acetone; ethers such as tetrahydrofuran, dioxane and diethyl ether; esters such as ethyl acetate; halogenated hydrocarbons such as dichloromethane; aromatic hydrocarbons such as chlorobenzene; or polar solvents such as N,N-dimethylformamide or acetic acid or their mixtures. Further, a mixture system of water and the foregoing solvent may be employed.

Although the quantity of the solvent is not particularly limited, normally the solvent is 5 to 20 times, by wt %, that of the compound (VII) is appropriate.

Examples of oxidant include aromatic peracids such as methachloroperbenzoic acid; aliphatic peracids such as acetyl hydroperoxide; or pertrifluoroacetate and hydrogen peroxide.

The products (II-2) can be isolated from the mixture of reactants by a usual method and can easily be purified by recrystallization or column chromatography.

Method B

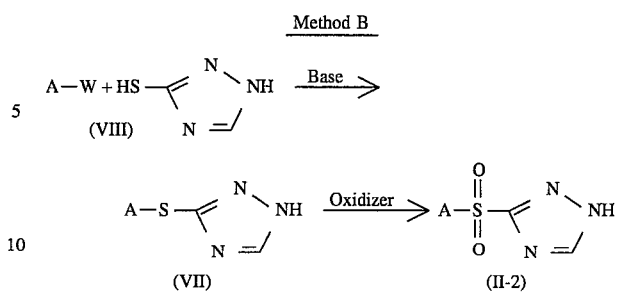

in which W is a halogen atom and A is the same as in general formula (I).

The compounds expressed by general formula (VII) can be obtained by causing the compounds expressed by general formula (VIII) and 3-mercapto-1,2,4-triazole to react with each other in an adequate solvent in the presence of a basic substance. Although the quantities of the materials are not particularly limited, 3-mercapto-1,2,4-triazole is preferably 1 to 1.2 equivalents with respect to 1 equivalent of the compound (VIII).

The reaction temperature may be arbitrarily determined so far as It ranges from a level realized by ice-cooling to the boiling point of the solvent. Although the reaction time varies depending upon the conditions, the reactions can usually be completed in 1 hour to 24 hours.

Examples of solvent may include: ketones such as acetone; ethers such as tetrahydrofuran, dioxane and diethyl ether; esters such as ethyl acetate; halogenated hydrocarbons such as dichloromethane; aromatic hydrocarbons such as chlorobenzene; or polar solvents such as N,N-dimethylformamide or acetic acid or their mixtures. Although the quantity of the solvent is not particularly limited, the quantity of the solvent is preferably 1.05 to 20 times, by wt %, the quantity of the compound (VIII).

Examples of basic materials include: inorganic bases such as sodium hydroxide, potassium hydroxide, sodium carbonate, potassium carbonate or sodium hydride; organic bases such as pyridine, triethylamine or N,N-diethyl aniline; and alkali metal alkoxides such as sodium methoxide or sodium ethoxide.

The products (VII) can be isolated from the mixture of reactants by a usual method and can easily be purified by recrystallization or column chromatography.

The compounds expressed by general formula (II-2) can be manufactured from the compounds expressed by general formula (VII) by a method similar to method A.

[II] FUNGICIDE

The fungicidal compositions according to the present invention contains a sulfamoyltriazole derivative expressed by general formula (I) as an effective component thereof.

When the compounds expressed by general formula (I) is used as the fungicide, they are mixed with a carrier, a diluent or an additive and an adjuvant by a known method while being formed into a formulation which is usually employed as agricultural chemicals, for example, powder material, granules, water-dispersible powder, emulsion, water soluble powder or flowable material. The compound may be mixed or used together with other agricultural chemicals, for example, fungicities, insecticides, miticides, herbicides, plant growth regulators, fertilizers and soil conditioners.

In particular, the mixed use with other fungicides can reduce the dosage of the compound, and therefore save labor. Further, the cooperative operation of the chemicals enlarges the fungicidal spectrum. In addition, the synergetic operation enables an ever greater effect to be obtained.

The carrier and the diluent may be normal solid or liquid carriers.

The solid carrier is exemplified by clay represented by the kaolinite group, montmorillonite group, illite group and polygorskite group. Specifically, it is exemplified by inorganic substances such as pyrophillite, attapulgite, sepeorite, kaolinite, bentonite, vermiculite, mica or talc; other inorganic substances such as gypsum, calcium carbonate, dolomite, diatomaceous earth, magnesium lime, apatite, zeolite, silicic anhydride or synthetic calcium silicate; vegetable organic substances such as soybean meal, tobacco flour, walnut flour, wheat flour, wood flour, starch or crystalline cellulose; synthetic or natural polymers such as coumarone resin, petroleum resin, alkyd resin, polyvinyl chloride, polyalkylene glycol, ketone resin, ester gum, covar gum or dammar gum; waxes such as carnauba wax or beeswax; and urea.

Examples of adequate liquid carriers include pararline- or naphthene-hydrocarbons such as kerosene, mineral oil, spindle oil or white oil: aromatic hydrocarbons such as xylene, ethyl benzene, cumene or methyl naphthalene; chlorinated hydrocarbons such as trichloroethylene, monochlorobenzene or ortho chlorotoluene; ethers such as dioxane or tetrahydrofuran; ketones such as acetone, methyl ethyl ketone, diisobutyl ketone, cyclohexanone, acetophenone or isophorone; esters such as ethyl acetate, amyl acetate, ethylene glycol acetate, diethylene glycol acetate, dibutyl maleate or diethyl succinate; alcohols such as methanol, n-hexanol, ethylene glycol, diethylene glycol, cyclohexanol or benzyl alcohol; ether alcohols such as ethylene glycol ethyl ether or diethylene glycol butyl ether; polar solvents such as dimethyl formamide or dimethyl sulfoxide; and water.

Further, a surface active agent and another adjuvant may be added to emulsificate, disperse, wet, spread, develop, bond, regulate degradation, stabilize the effective components, improve the fluidity, prevent corrosion and prevent freezing.

The surface active agent may be a nonionic compound, an anion compound, a cation compound or a dipolar compound. A nonionic and/or cation compound is usually employed.

Appropriate nonionic surface active agents include; compounds prepared by polymerizing and adding ethylene oxide to a higher alcohol, such as lauryl alcohol, stearyl alcohol or oleyl alcohol: compounds prepared by polymerizing and adding ethylene oxide to alkyl naphthol such as butyl naphthol or octyl naphthol; compounds prepared by polymerizing and adding ethylene oxide to a higher fatty acid such as palmitic acid, stearic acid or oleic acid; higher fatty acid esters of a polyatomic alcohol such as sorbitan; compounds prepared by polymerizing and adding ethylene oxide to the foregoing higher fatty acid ester; and compounds prepared by block-polymerizing ethylene oxide and propylene oxide.

The preferred cation surface active agents include: alkyl sulfonic ester salts such as sodium lauryl sulfate or oleyl alcohol sulfuric ester amine salt; alkyl sulfonates such as sulfone succinate dioctyl sodium ester or 2-ethyl hexene sodium sulfonate; and aryl sulfonates such as isopropyl naphthalene sodium sulfonate, methylene bisnapthalene sodium sulfonate, lignosulfonic sodium or dodecylbenzene sodium sulfonate.

In order to improve the characteristics of the fungicide and to enhance the effect thereof, polymers or other adjuvants such as casein, gelatin, albumin, glue, alginic soda, carboxylic methyl cellulose, methyl cellulose, hydroxyethyl cellulose or polyvinyl alcohol may be used.

The foregoing carriers and the various adjuvants may be arbitrarily used alone or in the form of a mixture to meet the desired object considering the system of formulation and the specific use.

Although the content of the compound according to the present invention in each of the foregoing prepared chemicals as an effective compound varies depending upon the formulation of the prepared chemicals, the preferred content is usually 0.1 wt % to 99 wt %, more preferably 1 wt % to 80 wt %.

In a water-dispersible powder according to the present invention, the compound serving as an effective component usually comprises 5% to 90% of the mixture with the solid carrier and dispersed wetting agent as a balance. If necessary, a protection colloid agent, an antifoaming agent and the like may be added.

In granule form according to the invention, the compound serving as an effective component usually comprises, for example, 1 wt % to 35 wt % of the mixture with the solid carrier and surface active agent as a balance. The compound serving as the effective component is uniformly mixed with the solid carrier or uniformly secured to or adsorbed in the surface of the solid carrier. The grain size is about 0.2 mm to 1.5 mm.

In an emulsion according to the invention, the compound serving as an effective component usually comprises, for example, 5 wt % to 30 wt % of the mixture with the emulsifier comprise about 5 wt % to 20 wt % and the balance composed of a liquid carrier. If necessary, a spreading agent and rust preventives may be added.

In a flowable material according to the invention, the compound serving as an effective component usually comprises, for example, 5 wt % to 50 wt % of the mixture with the disperse wetting agent comprise 3 wt % to 10 wt % and the balance composed of water. If necessary a protective collide agent, rust preventives and antifoaming agent may be added.

The sulfamoyltriazole derivative according to the present invention can be used as a fungicide in the form of the compound expressed by general formula (I) or in the form of any one of the foregoing formulations.

Although the concentration of the compound according to the present invention cannot be generalized because it varies depending upon the kind of plants to be used on, the application method, the formulation, and the application rate, the compound expressed by general formula (I) may be added by 0.1 ppm to 10,000 ppm to serve as the effective component when the compound is used in foliage treatment, preferably 1 ppm to 500 ppm. In soil treatment use, it may be contained by 10 g/ha to 100,000 g/ha, preferably 200 g/ha to 20,000 g/ha.

[EXAMPLES]

The present invention will now be described by providing examples.

(1) Synthesis of Precursor

Reference Example 1

Preparation of 3-(2,4,6-trimethylphenoxysulfonyl)-1,2,4-triazole 4.1 g of 2,4,6-trimethylphenol was dissolved in 15 ml of dichloromethane, and 4.2 ml of triethylamine was added while stirring the solution. Further, 4.6 g of 3-chlorosulfonyl-1,2,4-triazole was gradually added while being cooled with ice and stirred. Then, the solution was stirred at room temperature for 14 hours. After that, 2N hydrochloric acid was added to separate the components. The organic layer was washed with water, and then it was dried with magnesium sulfate. Then, the solvent was removed by distillation, so that coarse crystals were obtained. The coarse crystals were recrystallized from n-hexane/ethyl acetate, so that 3.0 g of the titled compound was obtained.

Reference Example 2

Preparation of 3-(3,3-dimethyl-2,3-dihydrobenzofuran-5-yloxysulfonyl)-1,2,4-triazole 5.4 g of 3,3-dimethyl-5-hydroxy-2,3-dihydrobenzofuran was dissolved in 30 ml of tetrahydrofuran, and then 4.6 ml of triethylamine was added while stirring the solution. Then, 5.0 g of 3-chlorosulfonyl-1,2,4-triazole was gradually added while cooling with ice and stirring the solution. Then, this was stirred for 14 hours. Tetrahydrofuran was evaporated, and 2N hydrochloric acid was added and extracted with ethyl acetate. The organic layer was washed with brine, dried with magnesium sulfate, and the solvent was removed, so that coarse crystals were obtained. This was then recrystallized from n-hexane/ethyl acetate, so that 2.7 g of the titled compound was obtained.

Reference Example 3

Preparation of 3-(2,4-dichloro-3-methylphenoxysulfonyl)-1,2,4-triazole 2.33 g of 2.4-dichloro-3-methylphenol was dissolved in 15 ml of tetrahydrofuran, and 1.84 ml of triethylamine was added while stirring the solution. Then, 2.0 g of 3-chlorosulfonyl-1,2,4-triazole was gradually added while cooling with ice and stirring the solution. Then, the solution was stirred at room temperature for 14 hours. Tetrahydrofuran was removed by distillation at reduced pressure, 2N hydrochloric acid was added, and extracted with ethyl acetate. The organic layer was washed with brine, and dried with magnesium sulfate. Then, the solvent was removed by distillation, so that coarse crystals were obtained. The coarse crystals were recrystallized from n-hexane/ethyl acetate, so that 2.25 g of the titled compound was obtained.

Reference Example 4

Preparation of 3-[4-(trifluoromethyl)phenylthiol-1,2,4-triazole (A) 62.4 ml of concentrated hydrochloric acid was dissolved in 45 ml of water, and 60 g of p-aminobenzotrifluoride was added. Then, 28.2 g of sodium nitrite dissolved in 60 ml of water was slowly dropped in at 5° C., and the solution was stirred for 30 minutes.

(B) 25.1 g of potassium hydroxide was dissolved in 100 ml of water, and 41.4 g of 3-mercapto-1,2,4-triazole was added.

The solution obtained in the process (B) was heated to 55° C., and the solution obtained in the process (A) was gradually added. Then, the resulting solution was stirred for 40 minutes. Chloroform was added to the reactant solution, and this was stirred for 20 minutes. Then, impurities were removed by filtration, and the chloroform layer was washed with water and brine. The organic layer was dried with magnesium sulfate, evaporated and a residue was purified by silica gel column chromatography. As a result, 47.2 g (yield was 52%) of the titled compound was obtained.

Reference Example 5

Preparation of 3-(4-nitrophenylthio)-1,2,4-triazole 5 g of 3-mercapto-1,2,4-triazole was dissolved in 40 ml of N,N-dimethylformamide, and 2.17 g of sodium hydride (60% in mineral oil) was added at 0° C.. The solution was stirred at the same temperature for one hour, and then 7.78 g of 1-chloro-4-nitrobenzene was added. The solution was stirred at room temperature for one hour, and refluxed for 2 hours. Then, 10% hydrochloric acid was added to the reactant solution, it was extracted with ethyl acetate. The organic layer was washed with brine, dried with magnesium sulfate, and the solvent was evaporated, so that coarse crystals were obtained. The coarse crystals were recrystallized from n-hexane/ethyl acetate, so that 7.72 g of the titled compound was obtained (at a yield of 66%).

Reference Example 6

Preparation of 3-[4-(trifluoromethyl)phenylsulfonyl]-1,2,4-triazole 76.4 g of 3-[4-(trifluoromethyl)phenylthio]-1,2,4-triazole synthesized by a method similar to that employed to prepare the precursor according to Reference Example 4 was dissolved in 400 ml of acetic acid, and 140 g of 30% hydrogen peroxide solution was added. Then, the temperature was gradually raised, and the solution was stirred at 100° C. for three hours. Then, the reactant solution was cooled to room temperature, and a water solution of sodium thiosulfate was added. Then, precipitate was filtered, so that 66.4 g of the titled compound was obtained (at a yield of 77%).

(2) Preparation of Sulfamoyl Triazole Derivative

Example 1

Preparation of 1-dimethylsulfamoyl-3-(3-trifluoromethylphenoxysulfonyl)-1,2,4-triazole (Compound No. 59)

1.0 g of 3-(3-trifluoromethylphenoxysulfonyl)-1,2,4-triazole synthesized by a method similar to that employed to prepare the precursor according to Reference Example 1 was dissolved in 10 ml of acetonitrile. Then, 0.57 g of potassium carbonate was added, and 0.59 g of dimethylsulfamoylchloride was gradually added at room temperature while stirring them. Then, they were refluxed for one hour, and the reactant solution was poured into water and extracted with ethyl acetate. The organic layer was washed with brine and dried with magnesium sulfate, and then the solvent was removed by distillation and the residue was purified by silica gel chromatography. As a result, 1.33 g of the titled compound was obtained.

Example 2

Preparation of 1-dimethylsulfamoyl-3-(4-trifluoromethylphenoxysulfonyl)-1,2,4-triazole (Compound No. 61).

1.0 g of 3-(4-trifluoromethylphenoxysulfonyl)-1,2,4-triazole synthesized by a method similar to that employed to prepare the precursor according to Reference Example 3 was dissolved in 10 ml of acetonitrile. Then, 0.57 g of potassium carbonate anhydride was added, and 0.59 g of dimethylsulfamoyl chloride was gradually added at room temperature while stirring the solution. The solution was then refluxed for one hour, and the reactant solution was poured into water and extracted with ethyl acetate. The organic layer was washed with brine and dried with magnesium sulfate, and then the solvent was removed by distillation and the residue was purified by silica gel chromatography. As a result, 1.18 g of the titled compound was obtained.

Example 3

Preparation of 1-dimethylsulfamoyl-3-(4-chloro-2-methylphenoxysulfonyl)-1,2,4-triazole (Compound No. 124)

0.57 g of 3-(4-chloro-2-methylphenoxysulfonyl)-1,2,4-triazole synthesized by a method similar to that employed to prepare the precursor according to Reference Example 1 was dissolved in 10 ml of acetonitrile, and 0.35 g of potassium carbonate was added, and 0.36 g of dimethylsulfamoylchloride was gradually added at room temperature while stirring the solution. The solution was then refluxed for one hour, and the reactant solution was poured into water and extracted with ethyl acetate. The organic layer was washed with brine and dried with magnesium sulfate. The solvent was removed by distillation, so that coarse crystals were obtained. This was recrystallized from n-hexane/ethyl acetate, so that 0.65 g of the titled compound was obtained.

Example 4

Preparation of 1-dimethylsulfamoyl-3-(2,4,6-trimethylphenoxysulfonyl)-1,2,4-triazole (Compound No. 192)

24.2 g of 3-(2,4,6-trimethylphenoxysulfonyl)-1,2,4-triazole was dissolved in 200 ml of acetonitrile, and 15.0 g of potassium carbonate was added, and 15.6 g of dimethylsulfamoylchloride was gradually added at room temperature while being stirred. Then, the solution was refluxed for one hour, and the reactant solution was poured into water and extracted with ethyl acetate. The organic layer was washed with brine and dried with magnesium sulfate. Then, the solvent was removed by distillation, so that coarse crystals were obtained. The coarse crystals were recrystallized from n-hexane/ethyl acetate, so that 30.94 g of the titled compound was obtained.

Example 5

Preparation of 1-dimethylsulfamoyl-3-(2,4,-dichloro-3-methylphenoxysulfonyl)-1,2,4-triazole (Compound No. 206)

1.0 g of 3-(2,4-dichloro-3-methylphenoxysulfonyl)-1,2,4-triazole synthesized by a method similar to that employed to prepare the precursor according to Reference Example 3 was dissolved in 15 ml of acetonitrile. Then, 0.54 g of potassium carbonate was added, and 0.56 g of dimethylsulfamoylchloride was gradually added at room temperature while being stirred. The solution was then refluxed for one hour, and the reactant solution was added and extracted with ethyl acetate. The organic layer was washed with brine and dried with magnesium sulfate. Then, the solvent was removed by distillation, so that coarse crystals were obtained. The coarse crystals were recrystallized from n-hexane/ethyl acetate, so that 1.05 g of the titled compound was obtained.

Example 6

Preparation of 1-dimethylsulfamoyl-3-(3,3-dimethyl-2,3-dihydrobenzofuran-5-yl-oxysulfonyl)-1,2,4-triazole (Compound No. 294)

1.00 g of 3-(3,3-dimethyl-2,3-dihydrobenzofuran-5-yl-oxysulfonyl)-1,2,4-triazole synthesized by a method similar to that employed to prepare the precursor according to Reference Example 2 was dissolved in 10 ml of acetonitrile. Then, 0.56 g of potassium carbonate was added, and 0.58 g of dimethylsulfamoylchloride was gradually added at room temperature while being stirred. The solution was then refluxed for one hour, and the reactant solution was poured into water and extracted with ethyl acetate. The organic layer was washed with brine and dried with magnesium sulfate, and then the solvent was removed by distillation, so that coarse crystals were obtained. The coarse crystals were recrystallized from n-hexane/ethyl acetate, so that 1.13 g of the titled compound was obtained.

Example 7

Preparation of 1-dimethylsulfamoyl-3-[4-(trifluoromethyl)phenylsulfonyl]-1,2,4-triazole (Compound No. 361)

66.4 g of 3-[4-(trifluoromethyl)phenylsulfonyl]-1,2,4-triazole synthesized by a method similar to that for preparing the precursor according to the Reference Example 6 was dissolved in 500 ml of acetonitrile. Then, 75.0 g of potassium carbonate was added, and 50.6 g of dimethylsulfamoylchloride was gradually added at room temperature while being stirred. The solution was then refluxed for two hours, and the reactant solution was poured into water and extracted with ethyl acetate. The organic layer was washed with brine and dried with magnesium sulfate, and then the solvent was evaporated, so that coarse crystals were obtained. The coarse crystals were recrystallized from n-hexane/ethyl acetate, so that 42.7 g of the titled compound was obtained (the yield was 47%).

The $^1$H-NMR peak values and the melting points of the substances according to the Examples and Reference Examples are shown in Table 12.

TABLE 12

| Compound No. | NMR δ (ppm) Solvent CDCl$_3$ | Melting point (°C.) |
| --- | --- | --- |
| 1 | 2.99(s, 6H), 7.1~7.4(m, 3H) | 117.0~118.4 |
| 23 | 1.18(s, 3H), 1.20(s, 3H), 3.05(s, 6H) 3.32(sep, 1H), 7.1~7.4(m, 4H), 8.71(s, 1H) | 77.4~80.6 |
| 37 | 3.05(s, 6H), 7.2~7.6(m, 4H), 8.69(s, 1H) | 117.8~119.6 |
| 39 | 3.03(s, 6H), 7.1~7.4(m, 4H), 8.65(s, 1H), 8.01(d, 2H), 8.75(s, 1H) | 101.1~102.9 |
| 41 | 3.03(s, 6H), 7.1~7.5(m, 4H), 8.63(s, 1H) | 139.6~141.6 |
| 47 | 3.02(s, 6H), 3.67(s, 3H), 6.7~7.5(m, 4H), 8.77(s, 1H) | 148.5~151.0 |
| 49 | 2.99(s, 6H), 3.74(s, 3H), 6.6~7.1(m, 4H), 8.59(s, 1H) | 74.5~76.1 |
| 59 | 3.01(s, 6H), 7.3~7.6(m, 4H), 8.59(s, 1H) | Oil |
| 61 | 3.01(s, 6H), 7.38, 7.61(ABq, 1H), 8.63 (s, 1H) | 125.8~127.5 |
| 81 | 3.04(s, 6H), 3.85(s, 3H), 7.26~7.96(m, 4H), 8.67(s, 1H) | 131.3~132.8 |
| 83 | 3.00(s, 66H), 3.87(s, 3H), 7.27, 7.99 (ABq, 4H), 8.60(s, 1H) | 127.7~130.0 |
| 89 | 3.06(s, 6H), 7.47, 8.20(ABq, 4H), 8.63 (s, 1H) | 139.4~141.7 |
| 91 | 3.11(s, 6H), 7.44~7.79(m, 4H), 8.63(s, 1H) | 135.2~137.6 |
| 93 | 3.08(s, 6H), 7.50~7.68(m, 4H), 8.72(s, 1H) | 136.9~139.6 |
| 95 | 3.07(s, 6H), 7.43, 7.72(ABq, 4H), 8.70 (s, 1H) | 184.9~188.3 |
| 101 | 2.25(s, 6H), 3.05(s, 6H), 7.03(s, 3H), 8.63(s, 1H) | 100.1~101.4 |
| 124 | 2.23(s, 3H), 3.00(s, 6H), 7.12(s, 2H) 8.55(s, 1H) | 96.0~97.3 |
| 136 | 3.02(s, 6H), 7.1~7.6(m, 3H), 8.63(s, 1H) | 116.7~119.3 |
| 140 | 3.06(s, 6H), 7.2~7.6(m, 3H), 8.65(s, 1H) | 128.5~130.8 |
| 152 | 3.03(s, 6H), 3.67(s, 6H), 6.3~7.2(m, 3H), 8.61(s, 1H) | 156.2~159.5 |
| 164 | 3.07(s, 6H), 7.5~7.8(m, 3H), 8.71(s, 1H) | 109.3~110.8 |
| 166 | 3.08(s, 6H), 7.5~7.65(m, 2H), 7.80(s, 1H), 8.72(s, 1H) | 117.6~120.0 |
| 192 | 2.22(s, 6H), 2.26(s, 3H), 3.08(s, 6H), 6.86(bs, 2H), 8.68(s, 1H) | 113.4~115.7 |
| 198 | 2.24(s, 3H), 2.34(s, 3H), 3.04(s, 6H), 8.59(s, 1H) | 131.5~133.5 |

TABLE 12-continued

| Compound No. | NMR δ (ppm) Solvent CDCl₃ | Melting point (°C.) |
|---|---|---|
| 206 | 2.44(s, 3H), 3.05(s, 6H), 7.28(s, 2H), 8.63(s, 1H) | 149.2–151.6 |
| 210 | 3.06(s, 6H), 7.42(s, 2H), 8.66(s, 1H) | 153.6–156.4 |
| 212 | 3.06(s, 6H), 7.28(s, 2H), 8.64(s, 1H) | 140.5–142.8 |
| 216 | 3.03(s, 6H), 7.33(s, 2H), 8.62(s, 1H) | 149.3–151.2 |
| 284 | 1.34(s, 6H), 3.00(s, 2H), 3.03(s, 6H), 6.5–7.2(m, 3H), 8.59(s, 1H) | 136.7–138.7 |
| 294 | 1.27(s, 6H), 3.00(s, 6H), 4.19(s, 2H), 6.5–7.2(m, 3H), 8.58(s, 1H) | 108.4–111.0 |
| 301 | 3.05(s, 6H), 7.55–7.75(m, 3H), 8.09–8.17(m, 2H), 8.58(s, 1H) | 126.1–128.5 |
| 310 | 2.68(s, 3H), 3.07(s, 6H), 7.34(d, 1H), 7.44(t, 1H), 7.58(dt, 1H), 8.25(dd, 1H), 8.60(s, 1H) | 113.6–114.0 |
| 312 | 2.45(s, 3H), 3.05(s, 6H), 7.42–7.55(m, 2H), 7.88–7.98(m, 2H), 8.58(s, 1H) | 102.1–102.4 |
| 314 | 2.46(s, 3H),3.06(s, 6H), 7.39(d, 2H), 7.88–7.98(m, 2H), 8.58(s, 1H) | 137.6–139.6 |
| 337 | 3.04(s, 6H), 7.48–7.70(m, 3H), 8.38 (dd, 1H), 8.62(s, 1H) | 133.0–134.8 |
| 339 | 3.07(s, 6H), 7.54(t, 1H), 7.61–7.70(m, 1H), 7.97–8.06(m, 1H), 8.07–8.15 (m, 1H), 8.61(s, 1H) | |
| 341 | 3.05(s, 6H), 7.57(d, 2H), 8.06(d, 2H), 8.60(s, 1H) | 122.5–124.2 |
| 357 | 3.03(s, 6H), 7.82–7.97(m, 3H), 8.55–8.64(m, 1H), 8.56(s, 1H) | 122.8–124.9 |
| 359 | 3.07(s, 6H), 7.77(t, 1H), 7.96(d, 1H), 8.34(d, 1H), 8.40(s, 1H), 8.61(s, 1H) | 122.5–123.7 |
| 361 | 3.07(s, 6H), 7.87(d, 2H), 8.28(d, 2H), 8.61(s, 1H) | 153.6–155.6 |
| 363 | 3.04(s, 6H), 6.50(t, 1H), 7.13–7.90(m, 3H), 8.25(dd, 1H), 8.56(s, 1H) | 105.8–108.0 |
| 389 | 2.95(s, 6H), 8.31(d, 2H), 8.48(d, 2H), 9.46(s, 1H) Solvent DMSO | 189.5–192.0 |
| 492 | 2.28(s, 3H), 2.68(s, 6H), 3.02(s, 6H), 6.90(s, 2H), 8.47(s, 1H) | 181.0–185.7 |
| 506 | 2.51(s, 3H), 3.05(s, 6H), 7.50(d, 1H), 8.11(d, 1H), 8.53(s, 1H) | 148.0–152.5 |
| 540 | 3.06(s, 6H), 8.07–8.53(m, 2H), 8.55(s, 1H), 8.88(bs, 1H) | 139.4–142.7 |
| 610 | 3.05(s, 6H), 8.09(bs, 1H), 8.57(bs, 1H), 8.61(s, 1H) | 137.5–139.5 |

Formulation examples of chemicals using the compounds according to the present invention will now be described. The "parts" used below means parts by weight.

Example Chemical 1 (Emulsion)

| | |
|---|---|
| Compound No. 192 | 10 |
| Xylene | 45 |
| Dodecylbenzenesulfonic acid calcium | 7 |
| Polyoxy ethylene styrylphenyl ether | 13 |
| dimethylformamide | 25 |

The foregoing materials were uniformly mixed and dissolved, so that 100 parts of emulsion were obtained.

Example Chemical 2 (Water-Dispersible-Powder)

| | |
|---|---|
| Compound No. 361 | 20 |
| Diatomaceous earth | 70 |
| Lignosulfonic acid calcium | 5 |
| Naphthalenesulfonic acid formalin condensate | 5 |

The foregoing materials were mixed and crushed, so that 100 parts of water-dispersible-powder were obtained.

Example Chemical 3 (Granules)

| | |
|---|---|
| Compound No. 192 | 5 |
| Bentonite | 50 |
| Talc | 42 |
| Lignosulfonic acid soda | 2 |
| Polyoxyethylenealkylaryl ether | 1 |

The foregoing materials were mixed sufficiently, and water is added in an adequate quantity as to be kneaded. Then, an extruding granulator was used, so that 100 parts of granule were obtained.

Example Chemical 4 (Flowable Agent)

| | |
|---|---|
| Compound No. 361 | 30 |
| Sulfosuccinate di-2-ethylhexylester sodium salt | 2 |
| Polyoxyethylenenonylphenylether | 3 |
| Antifoaming agent | 1 |
| Propylene glycol | 5 |
| Water | 59 |

The foregoing materials were crushed and uniformly mixed by using a wet-type ball mill, so that 100 parts of flowable agent were obtained.

[Efficiency Test Examples of The Fungicide]

Effects of preventing and curing crop damage obtainable from the fungicide according to the present invention will now be specifically described.

The compound according to the present invention and the fungicide containing same have excellent effects in preventing and curing the following various crop diseases caused from Oomycetes: grape downy mildew (*Plasmopara viticola*), gourd downy mildew (*Pseudoperonospora cubensis*), damping-off type disease (*Phytophthora melonis*), phytophora blight (*Phytophthora capsici*), late blight (*Phytophthora infestans*), rape vegetable downy mildew (*Peronospora brassicae*), Welsh onion downy mildew (*Peronospora destructor*), spinach downy mildew (*Peronospor spinaciae*), soybean downy mildew (*Peronospora manshurica*), broad bean downy mildew (*Peronospora viciae*), tobacco disease (*Phytophthora nicotiana var. nicotiana*), potato disease (*Phytophthora infestaris*), hop disease (*Pseudoperonospora humuli*), pineapple disease (*Phytophthora cinnamomi*), green pepper disease (*Phytophthora capsici*), strawberry root rot (*Phytophthora fragarie*) and various damping-off type diseases (caused from Pythium group germs).

The results of the following tests were evaluated in such a manner that the degree of crop damages were examined in accordance with the following reference seven days after the inoculation of disease-causing germs and the severity and the preventive value were obtained by the following equations.

| Evaluation | Degree of Disease |
|---|---|
| Excellent | No disease found |
| Good | Lesion area was less than ⅓ |
| Allowable | Lesion area was ⅓ to less than ⅔ |
| No Good | Disease area was ⅔ or more |

$$\text{Disease Ratio (\%)} = \frac{(n^0 \times 0) + (n^1 \times 1) + (n^2 \times 2) + (n^3 \times 3)}{3N} \times 100$$

where $n^0$: No of leaves in which the degree of disease was Excellent $n^1$: No of leaves in which the degree of disease was Good.
$n^2$: No of leaves in which the degree of disease was Allowable
$n^3$: No of leaves in which the degree of disease was No Good.
N: $n^0+n^1+n^2+n^3$ Preventive value (%) =

$$\left(1 - \frac{\text{severity in treated regions}}{\text{severity in non-treated regions}}\right) \times 100$$

The test results were evaluated in accordance with the following criteria.

| | Criteria |
|---|---|
| A: | Preventive value was 95% or higher |
| B: | Preventive value was 80% to lower than 95% |
| C: | Preventive value was 50% to lower than 80% |
| D: | Preventive value was lower than 50% |

Test Example 1

Test to evaluate the effect of preventing cucumber downy mildew

Five seeds of cucumber (variety: Sagami Hanshiro) were seeded in vinyl chloride pots each having a diameter of 9 cm and cultivated in a greenhouse for seven days. The water-dispersible powder according to Example Chemical 2 was diluted with water to obtain a concentration of effective component of 200 ppm, 10 ml of this was sprayed on each seedling of cucumbers having spread cotyledons. One day after spraying, a globule suspension of cucumber downy mildew (*Pseudoperonospora cubensis*) was inoculated by atomization. The seedlings were allowed to stand in a wet room at 20° C. for one day. Then, the seedlings were transferred and Brown in a greenhouse so as to observe the degree of disease. The results of the evaluations are shown in Table 13.

TABLE 13

| Compound No. | Grade | Compound No. | Grade |
|---|---|---|---|
| 1 | A | 301 | A |
| 37 | A | 310 | A |
| 41 | B | 312 | A |
| 49 | A | 314 | A |
| 59 | A | 337 | A |
| 61 | A | 339 | A |
| 83 | B | 341 | A |
| 89 | B | 357 | A |
| 101 | A | 359 | A |
| 124 | A | 361 | A |
| 192 | A | 363 | B |
| 206 | A | 389 | D |
| 216 | A | 492 | C |
| 284 | B | 502 | D |
| 294 | A | 610 | B |

Test Example 2

Test to evaluate the effect of preventing potato disease

The water-dispersible powder according to Example Chemical 2 was diluted with water to obtain a concentration of effective component of 200 ppm and 10 ml of this was sprayed on each leaf of the potatoes (variety: Meikuin). One day after spraying, a globule suspension of potato disease (*Phytophthora infestans*) was inoculated by atomization. The seedlings were allowed to stand in a wet room at 17° C. for one day. Then, the seedlings were transferred and grown in a greenhouse so as to observe the degree of disease. The results of the evaluations are shown in Table 14.

TABLE 14

| Compounds No. | Evaluation |
|---|---|
| 61 | A |
| 206 | A |

(Effect of the Invention)

The compound expressed by general formula (I) is characterized by a structure in which the specific aryl group is bonded to the 1-sulfamoyl-1,2,4-triazole ring while interposing the sulfonyl group. The characterized structure is considered to cause the sulfamoyltriazole derivative to exhibit the excellent fungicidal performance.

What is claimed is:

1. A sulfamoyltriazole derivative expressed by formula (I):

$$A{-}(O)_l{-}\underset{\underset{O}{\|}}{\overset{\overset{O}{\|}}{S}}{-}\underset{N=\!\!/}{\overset{N\diagdown}{\diagup}}{-}N{-}\underset{\underset{O}{\|}}{\overset{\overset{O}{\|}}{S}}{-}N\diagup\diagdown\overset{R^1}{\underset{R^2}{}} \quad (I)$$

in which $R^1$ and $R^2$ are the same or different lower alkyl groups or an alkylene chain formed by integrating $R^1$ and $R^2$ and having 3 to 6 carbon atoms which may be substituted by a lower alkyl group; l is 1; and A is expressed by any one of the following substituents:

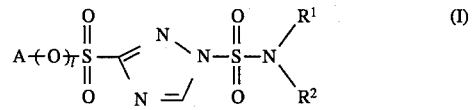

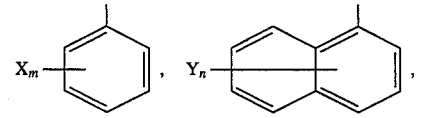

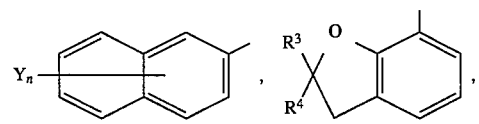

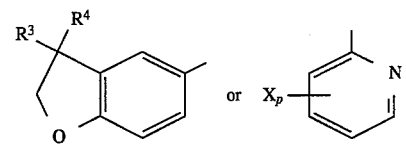

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is an integer 1, 2, 3, 4 or 5, Y is a hydrogen atom, a halogen atom, a lower alkyl group, a lower alkenyl group, a lower alkoxy group, a lower haloalkyl group, a lower haloalkoxy group, a lower alkylcarbonyl group, a formyl group, a lower alkoxycarbonyl group, a nitro group, a cyano group or an acetylamino group; n is an integer 1, 2, 3, 4 or 5; $R^3$ and $R^4$ are the same or different hydrogen atoms or lower alkyl groups; and p is an integer 1, 2, 3 or 4.

2. A sulfamoyltriazole derivative according to claim 1 wherein A is expressed by any one of the following substituents:

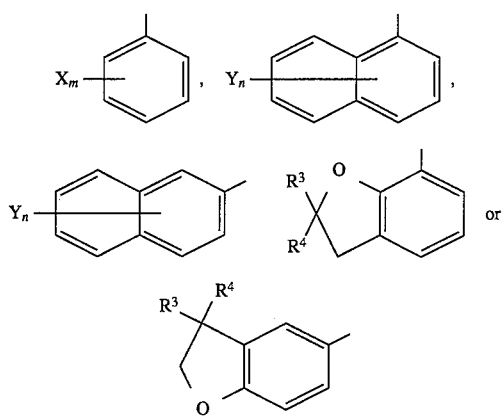

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is an integer 1, 2, 3, 4 or 5, Y is a hydrogen atom, a halogen atom, a lower alkyl group, a lower alkenyl group, a lower alkoxy group, a lower haloalkyl group, a lower haloalkoxy group, a lower alkylcarbonyl group, a formyl group, a lower alkoxycarbonyl group, a nitro group, a cyano group or an acetylamino group; n is an integer 1, 2, 3, 4 or 5; and $R^3$ and $R^4$ are the same or different hydrogen atoms or lower alkyl groups.

3. A sulfamoyltriazole derivative according to claim 1 wherein A in formula (I) is expressed by the following formula:

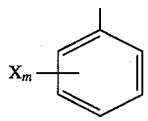

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is an integer 1, 2, 3, 4 or 5.

4. A fungicidal composition containing a sulfamoyltriazole derivative expressed by formula (I) as an effective component:

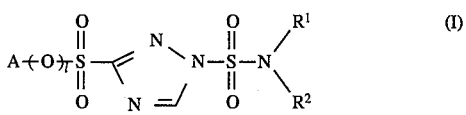

in which $R^1$ and $R^2$ are the same or different lower alkyl groups or an alkylene chain formed by integrating $R^1$ and $R^2$ and having 3 to 6 carbon atoms which may be substituted by a lower alkyl group; l is 0; and A is expressed by any one of the following substituents:

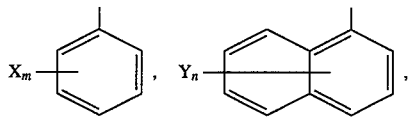

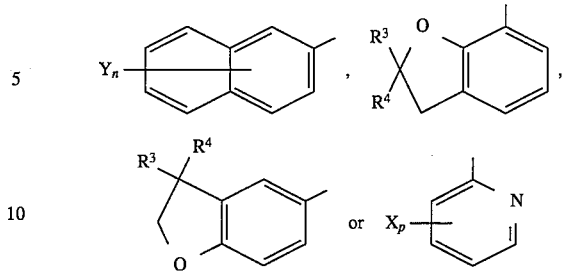

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is 1, 2, 3, 4 or 5, Y is a hydrogen atom, a halogen atom, a lower alkyl group, a lower alkenyl group, a lower alkoxy group, a lower haloalkyl group, a lower haloalkoxy group, a lower alkylcarbonyl group, a formyl group, a lower alkoxycarbonyl group, a nitro group, a cyano group or an acetylamino group; n is 1, 2, 3, 4 or 5; $R^3$ and $R^4$ are the same or different hydrogen atoms or lower alkyl groups; and p is 1, 2, 3 or 4 together with an agriculturally acceptable carrier, diluent, additive and/or adjuvant.

5. A fungicidal composition according to claim 4 wherein l in formula (I) is 1 and A is expressed by any one of the following substituents:

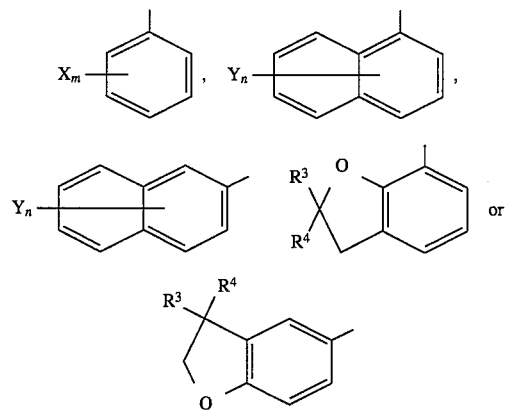

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is an integer 1, 2, 3,4 or 5, Y is a hydrogen atom, a halogen atom, a lower alkyl group, a lower alkenyl group, a lower alkoxy group, a lower haloalkyl group, a lower haloalkoxy group, a lower alkylcarbonyl group, a formyl group, a lower alkoxycarbonyl group, a nitro group, a cyano group or an acetylamino group; n is an integer 1, 2, 3, 4 or 5; and $R^3$ and $R^4$ are the same or different hydrogen atoms or lower alkyl groups.

6. A fungicidal composition according to claim 4 wherein A in formula (I) is expressed by the following formula:

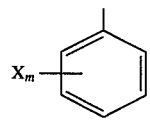

in which X is a hydrogen atom, a halogen atom, a lower alkyl group, a lower alkenyl group, a lower alkoxy group, a lower haloalkyl group, a lower haloalkoxy group, a lower alkylcarbonyl group, a phenyl group, a phenoxy group, a benzyl group, a benzyloxy group, a formyl group, a lower alkoxycarbonyl group, a nitro group, a cyano group or an acetylamino group; m is an integer 1, 2, 3, 4 or 5.

7. A sulfamoyltriazole derivative according to claim 1, which is 1-dimethylsulfamoyl-3-(2,4-dichloro-3-methylphenoxysulfonyl)-1,2,4-triazole.

8. The composition as claimed in claim 4, wherein the sulfamoyltriazole derivative of formula (1) is present in a fungicidally effective amount.

* * * * *

UNITED STATES PATENT AND TRADEMARK OFFICE
CERTIFICATE OF CORRECTION

PATENT NO. : 5,527,818
DATED : June 18, 1996
INVENTOR(S) : Atsushi GOH, et al.

It is certified that error appears in the above-indentified patent and that said Letters Patent is hereby corrected as shown below:

Title page, & col. 1, line 1, Items [54] and [86], the Title and PCT information, should read:

-- [54] SULFAMOYLTRIAZOLE DERIVATIVES AND FUNGICIDAL COMPOSITION CONTAINING SAME AS EFFECTIVE COMPONENT THEREOF --

The listed PCT data should read as follows:
-- [86] PCT No: PCT/JP93/00939
§ 371 Date: Mar. 3, 1994
§ 102 (e) Date: Mar. 3, 1994. --

Signed and Sealed this

Eighth Day of October, 1996

Attest:

BRUCE LEHMAN

Attesting Officer     Commissioner of Patents and Trademarks